United States Patent
Choi (10) Patent No.: US 11,998,341 B2
(45) Date of Patent: Jun. 4, 2024

(54) APPARATUS, METHOD, AND COMPUTER-READABLE RECORDING MEDIUM FOR MEASURING SIZE OF ELECTROCARDIOGRAPHY SIGNAL USING ELECTROCARDIOGRAPHY SIGNAL USING HILBERT TRANSFORM

(71) Applicant: Man-Rim Choi, Busan (KR)

(72) Inventor: Man-Rim Choi, Busan (KR)

(*) Notice: Subject to any disclaimer, the term of this patent is extended or adjusted under 35 U.S.C. 154(b) by 379 days.

(21) Appl. No.: 17/438,154

(22) PCT Filed: Mar. 11, 2019

(86) PCT No.: PCT/KR2019/002805
§ 371 (c)(1),
(2) Date: Sep. 10, 2021

(87) PCT Pub. No.: WO2020/184749
PCT Pub. Date: Sep. 17, 2020

(65) Prior Publication Data
US 2022/0142549 A1    May 12, 2022

(51) Int. Cl.
*A61B 5/349* (2021.01)
*A61B 5/318* (2021.01)
*A61B 5/352* (2021.01)
*A61B 5/353* (2021.01)
*A61B 5/355* (2021.01)

(52) U.S. Cl.
CPC .............. *A61B 5/349* (2021.01); *A61B 5/318* (2021.01); *A61B 5/352* (2021.01); *A61B 5/353* (2021.01); *A61B 5/355* (2021.01)

(58) Field of Classification Search
CPC ......... A61B 5/349; A61B 5/355; A61B 5/353; A61B 5/318; A61B 5/352
See application file for complete search history.

(56) References Cited

U.S. PATENT DOCUMENTS

| | | | |
|---|---|---|---|
| 7,729,753 B2 | 6/2010 | Kremliovsky et al. | |
| 2003/0233050 A1* | 12/2003 | Haghighi-Mood | A61B 5/349 600/515 |
| 2005/0107836 A1 | 5/2005 | Noren | |
| 2006/0084881 A1 | 4/2006 | Korzinov | |
| 2007/0219453 A1 | 9/2007 | Kremliovsky et al. | |
| 2016/0220128 A1 | 8/2016 | Den Brinker et al. | |
| 2019/0175120 A1* | 6/2019 | Huang | A61B 5/72 |

FOREIGN PATENT DOCUMENTS

| | | | |
|---|---|---|---|
| JP | 2010510581 A | 4/2010 | |
| JP | 2016-538005 A | 12/2016 | |
| KR | 10-2002-7011582 A | 9/2002 | |

(Continued)

*Primary Examiner* — Catherine M Voorhees
*Assistant Examiner* — Roland Dinga
(74) *Attorney, Agent, or Firm* — Maschoff Brennan (57) ABSTRACT

An apparatus for measuring the size of an electrocardiography signal using a Hilbert transform, according to one embodiment of the present invention, may comprise: a receiving unit for receiving a measured electrocardiography signal; a transform unit for Hilbert-transforming the received electrocardiography signal; and a measurement unit for obtaining the size of the electrocardiography signal on the basis of the Hilbert-transformed electrocardiography signal.

6 Claims, 5 Drawing Sheets

(56) References Cited

FOREIGN PATENT DOCUMENTS

| KR | 10-2003-0011785 A | 2/2003 |
|----|-------------------|--------|
| KR | 10-2014-0112010 A | 9/2014 |
| KR | 2014-0144132      | 12/2014 |
| KR | 10-2016-0053395 A | 5/2016 |
| KR | 10-2014-0152009 A | 4/2017 |

* cited by examiner

APPARATUS, METHOD, AND COMPUTER-READABLE RECORDING MEDIUM FOR MEASURING SIZE OF ELECTROCARDIOGRAPHY SIGNAL USING ELECTROCARDIOGRAPHY SIGNAL USING HILBERT TRANSFORM

TECHNICAL FIELD

The present disclosure relates to an apparatus, a method, and a computer-readable recording medium for measuring a size of an electrocardiography signal using a Hilbert transform.

BACKGROUND ART

Electrocardiography (ECG) signals are used to extract an image inside a body at a specific time point as well as image information in diagnosis using medical images (ultrasound, MT, and CT).

Figure 1A:
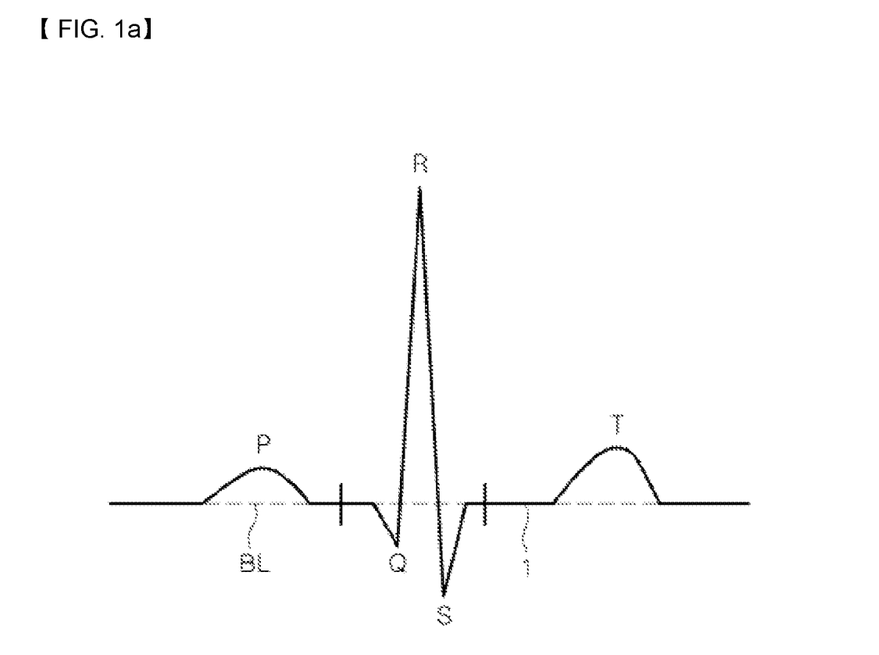
FIG. 1a is a view showing a general electrocardiography signal.

As shown in FIG. 1a, a waveform of an electrocardiography signal 1 may be displayed as a curve representing a current and a potential difference generated by contraction of a heart based on a baseline BL. In general, a P wave, a Q wave, an R wave, an S wave, and a T wave are consecutively generated within one cycle of the electrocardiography signal 1. The P wave is a characteristic representing contraction of an atrium, a series of the Q, R, and S waves (QRS complex) is a characteristic representing contraction of a ventricle, and the T wave is a characteristic representing relaxation of the ventricle.

For health monitoring using electrocardiography, sizes of the P, R, and T waves among electrocardiography signals are very important factors. However, there is no international regulation for measurement of the sizes of the P, R, and T waves by relevant societies or institutions.

In general, as shown in FIG. 1a, the sizes of the P, R, and T waves refer to heights from the baseline BL to peaks of the P, R, and T waves, respectively, and the size of the R wave may refer to a height from a peak having a lower value between peaks of the Q and S waves to the peak of the R wave.

Figure 1B:
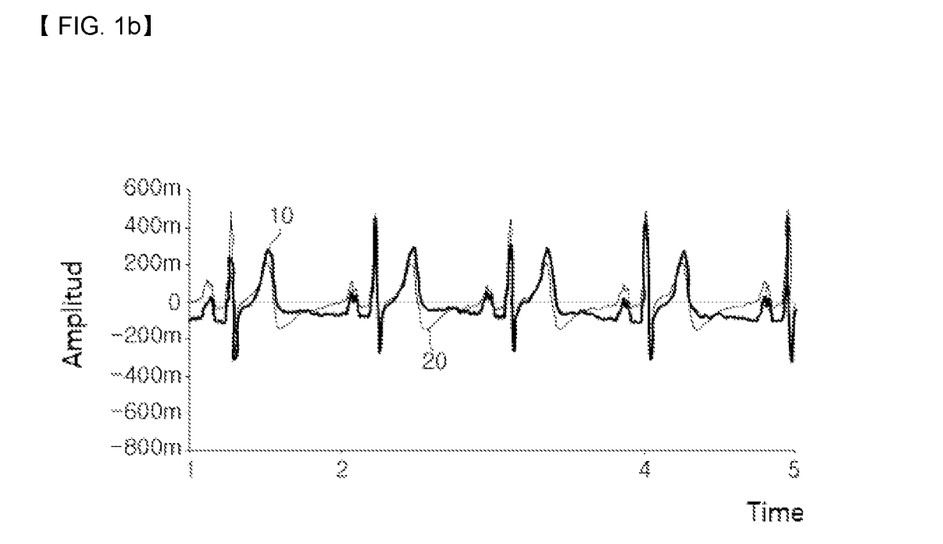
FIG. 1b is a view showing an electrocardiography signal including noise and an electrocardiography signal from which the noise is removed.

However, as shown in FIG. 1b, since the baseline BL of the electrocardiography signal 1 is greatly affected by low-frequency or high-frequency noise, when the sizes of the P, R, and T waves are measured based on the baseline BL, it is difficult to obtain the sizes of the P, R, and T waves with high reliability. In FIG. 1b described above, a reference numeral 10 denotes an electrocardiography signal including noise, and a reference numeral 20 denotes an electrocardiography signal from which the noise is removed by using a high-pass filter of 0.67 Hz.

As the related art, there is Korean Unexamined Patent Publication No. 2014-0144132 ("Method for Detecting Electrocardiogram Signal, Method for Displaying Electrocardiogram Signal, and Electrocardiogram Signal Detecting Apparatus", Dec. 18, 2014).

DETAILED DESCRIPTION OF THE INVENTION

Technical Problem

According to one embodiment of the present invention, there is provided an apparatus, a method, and a computer-readable recording medium for measuring a size of an electrocardiography signal using a Hilbert transform, capable of obtaining sizes of P, R, and T waves with high reliability.

Technical Solution

According to a first embodiment of the present invention, there is provided an apparatus for measuring a size of an electrocardiography signal using a Hilbert transform, the apparatus including: a receiving unit for receiving a measured electrocardiography signal; a transform unit for Hilbert-transforming the received electrocardiography signal; and a measurement unit for obtaining the size of the electrocardiography signal based on the Hilbert-transformed electrocardiography signal.

According to one embodiment of the present invention, the measurement unit may include: a first module for creating a Nyquist diagram, which is a time response curve in which a value of the electrocardiography signal is a real value and a value of the Hilbert-transformed electrocardiography signal is an imaginary value; a second module for fitting the created Nyquist diagram by using circle fitting; and a third module for obtaining a diameter of a circle formed on the fitted Nyquist diagram as the size of the electrocardiography signal.

According to one embodiment of the present invention, the diameter of the circle formed on the fitted Nyquist diagram may be proportional to sizes of a P wave, an R wave, and a T wave of the electrocardiography signal.

According to one embodiment of the present invention, the third module may be configured to: obtain a diameter of a first circle corresponding to a first curve shape formed at an earliest time among curve shapes included in the Nyquist diagram as a size of a P wave of the electrocardiography signal; obtain a diameter of a second circle corresponding to a second curve shape formed at a later time than the first curve shape as a size of an R wave of the electrocardiography signal; and obtain a diameter of a third circle corresponding to a third curve shape formed at a later time than the second curve shape as a size of a T wave of the electrocardiography signal.

According to one embodiment of the present invention, the size of the P or T wave may be a height from a baseline of the electrocardiography signal to a peak of the P or T wave, and the size of the R wave may be a height from a peak having a lower value between peaks of Q and S waves to a peak of the R wave.

According to a second embodiment of the present invention, there is provided a method for measuring a size of an electrocardiography signal using a Hilbert transform, the method including: a first step of receiving, by a receiving unit, a measured electrocardiography signal; a second step of Hilbert-transforming, by a transform unit, the received electrocardiography signal; and a third step of obtaining, by a measurement unit, the size of the electrocardiography signal based on the Hilbert-transformed electrocardiography signal.

According to a third embodiment of the present invention, there is provided a computer-readable recording medium recorded with a program to execute the method for measuring the size of the electrocardiography signal using the Hilbert transform.

Advantageous Effects

According to one embodiment of the present invention, the electrocardiography signal is Hilbert-transformed, and the size of the electrocardiography signal is obtained based on the Hilbert-transformed electrocardiography signal, so that the sizes of the P, R, and T waves can be obtained with higher reliability than a scheme of obtaining sizes of P, R, and T waves by using a baseline BL.

BEST MODE

Embodiments of the present invention may be modified into various other forms, and the scope of the present invention is not limited only to the following embodiments. In the drawings, shapes, sizes, and the like of elements may be exaggerated for a clearer description, and elements denoted by the same reference numerals in the drawings are the same elements.

Figure 2:
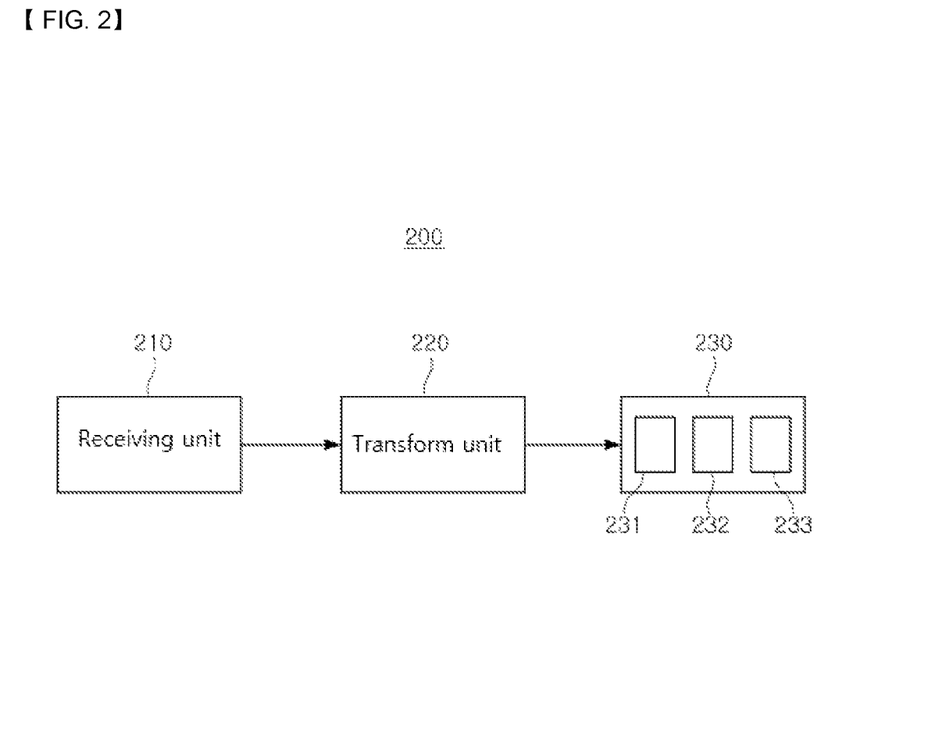
FIG. 2 is a block diagram showing an apparatus for measuring a size of an electrocardiography signal using a Hilbert transform according to one embodiment of the present invention.
Figure 3A:
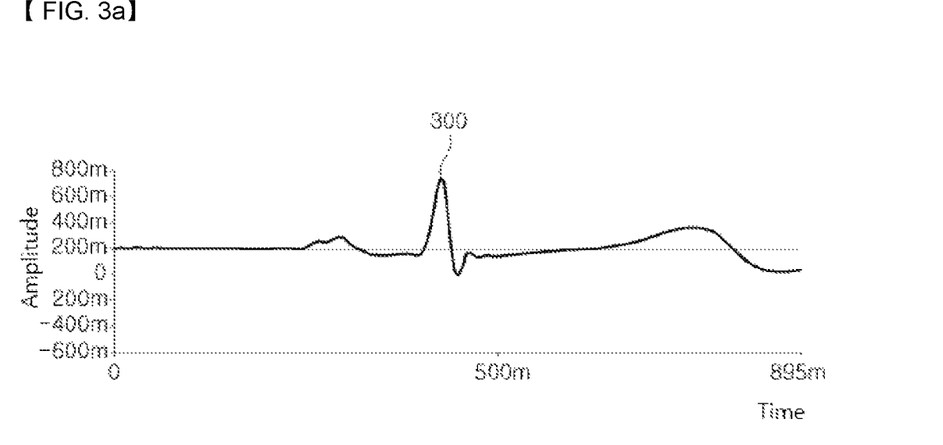
FIG. 3a is a view showing an electrocardiography signal.
Figure 3B:
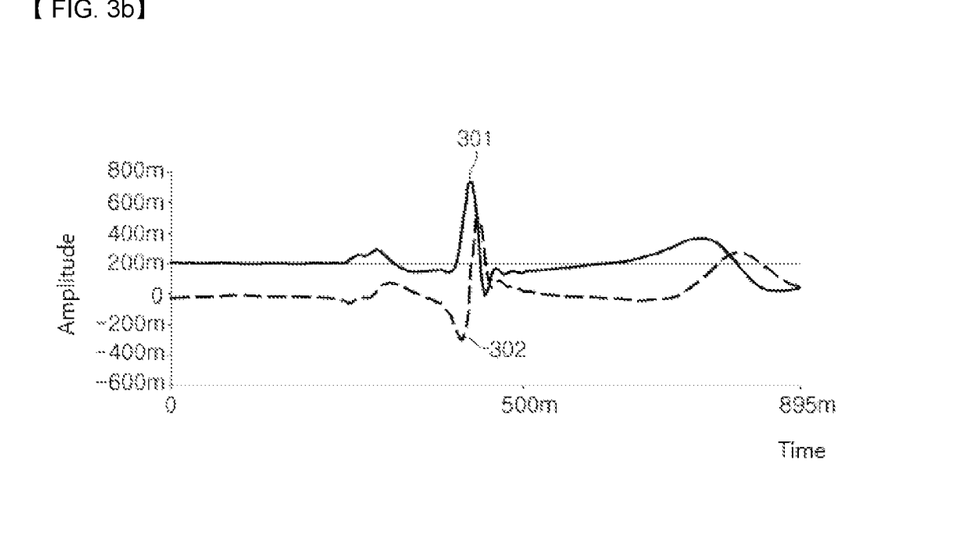
FIG. 3b is a view showing a comparison between an electrocardiography signal and a Hilbert-transformed electrocardiography signal.
Figure 3C:
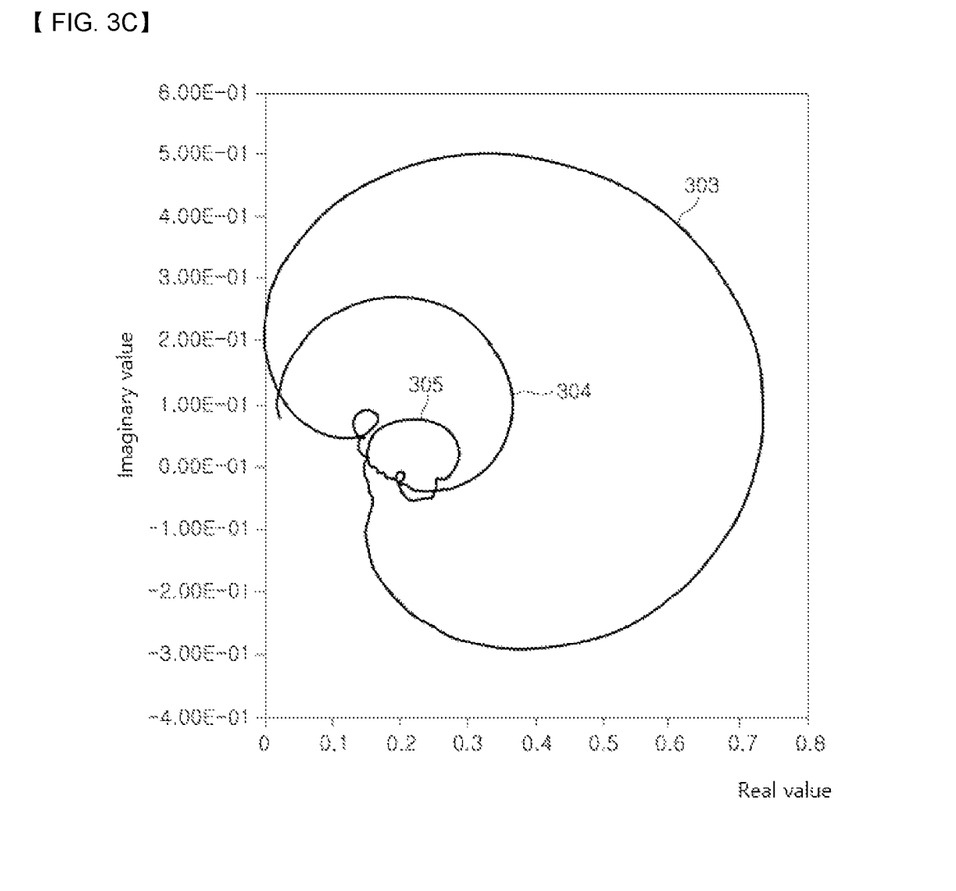
FIG. 3c is a view showing a Nyquist diagram created such that a value of an electrocardiography signal is a real value and a value of a Hilbert-transformed electrocardiography signal is an imaginary value.
Figure 3D:
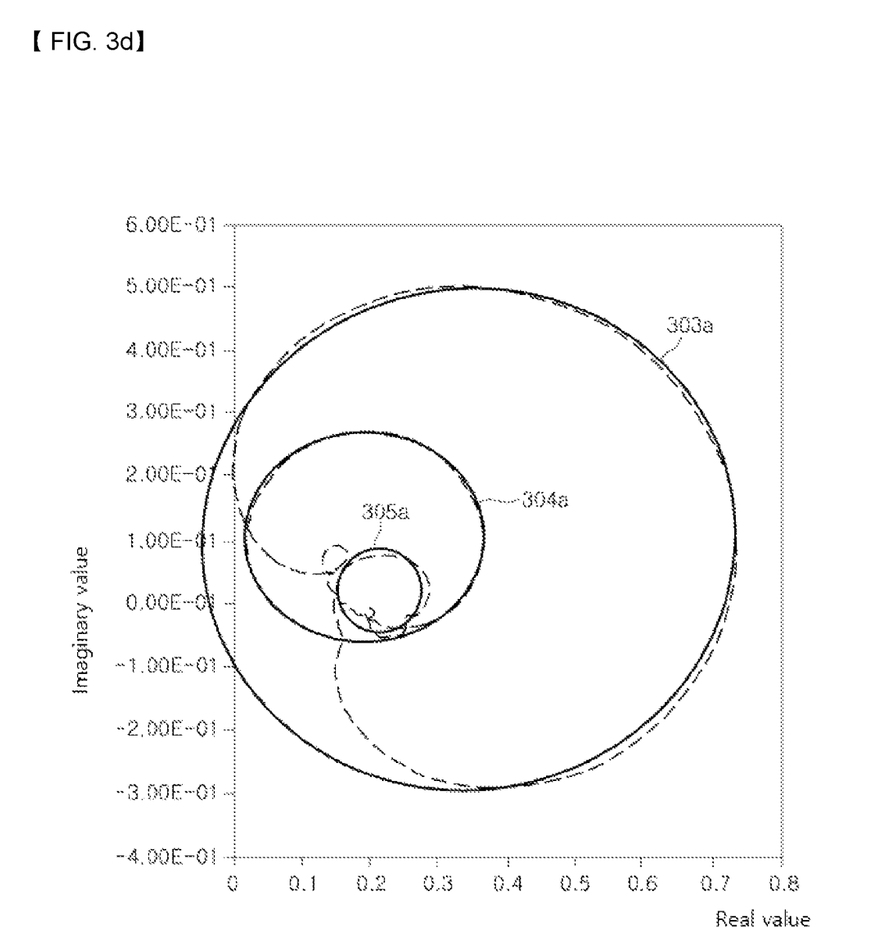
FIG. 3d is a view for describing a process of obtaining a size of the electrocardiography signal from a Nyquist diagram fitted by using circle fitting.

FIG. 2 is a block diagram showing an apparatus for measuring a size of an electrocardiography signal using a Hilbert transform according to one embodiment of the present invention. In addition, FIG. 3a is a view showing an electrocardiography signal, and FIG. 3b is a view showing a comparison between an electrocardiography signal and a Hilbert-transformed electrocardiography signal. Meanwhile, FIG. 3c is a view showing a Nyquist diagram created such that a value of an electrocardiography signal is a real value and a value of a Hilbert-transformed electrocardiography signal is an imaginary value, and FIG. 3d is a view for describing a process of obtaining a size of the electrocardiography signal from a Nyquist diagram fitted by using circle fitting.

First, as shown in FIG. 2, according to one embodiment of the present invention, an apparatus 200 for measuring a size of an electrocardiography signal using a Hilbert transform may include: a receiving unit 210 for receiving a measured electrocardiography signal; a transform unit 220 for Hilbert-transforming the received electrocardiography signal; and a measurement unit 230 for obtaining the size of the electrocardiography signal based on the Hilbert-transformed electrocardiography signal.

In detail, the receiving unit 210 may receive the measured electrocardiography signal from an outside, and transmit the received electrocardiography signal to the transform unit 220.

The transform unit 220 may Hilbert-transform the electrocardiography signal received from the receiving unit 210.

The Hilbert transform may shift only a phase of the electrocardiography signal by $+\pi/2$ at a negative frequency and by $-\pi/2$ at a positive frequency, while maintaining the size (amplitude) of the electrocardiography signal. Real signals may be extended to a complex dimension, so that analysis of sizes and the phases may be facilitated. In other words, when a predetermined real signal is x(t), and a Hilbert-transformed signal is x̂(t), a signal extended to a complex dimension may be obtained as $x_p(t)=x(t)+j\hat{x}(t)$.

FIG. 3a is a view illustrating an electrocardiography signal 300, and FIG. 3b is a view showing a comparison between the electrocardiography signal 301 and a Hilbert-transformed electrocardiography signal 302.

Next, the measurement unit 230 may obtain the size of the electrocardiography signal based on the Hilbert-transformed electrocardiography signal. To this end, the measurement unit 230 may include a first module 231, a second module 232, and a third module 233.

The first module 231 may create a Nyquist diagram, which is a time response curve in which a value of the electrocardiography signal is a real value and a value of the Hilbert-transformed electrocardiography signal is an imaginary value. The created Nyquist diagram may be transmitted to the second module 232. It should be noted that while a Nyquist diagram generally refers to a frequency response curve according to a frequency variation, the Nyquist diagram in the present invention refers to a time response curve according to a time variation.

FIG. 3c is a view showing a Nyquist diagram created such that a value of an electrocardiography signal is a real value and a value of a Hilbert-transformed electrocardiography signal is an imaginary value. It may be found from the Nyquist diagram of FIG. 3c that three curve shapes 303, 304, and 305 having mutually different diameters are formed.

In other words, when the Nyquist diagram is created such that the value of the electrocardiography signal is the real value and the value of the Hilbert-transformed electrocardiography signal is the imaginary value, as a time passes, a first curve shape 305, a second curve shape 303, and a third curve shape 304 may be sequentially formed. This is because the electrocardiography signal appears in an order of a P wave, an R wave, and a T wave. In this case, the first curve shape 305 may correspond to a first circle 305a that will be described below, the second curve shape 303 may correspond to a second circle 303a that will be described below, and the third curve shape 304 may correspond to a third circle 304a that will be described below.

The second module 232 may fit the created Nyquist diagram by using circle fitting.

FIG. 3d is a view showing a Nyquist diagram fitted by using circle fitting. As shown in FIG. 3d, three circles 303a, 304a, and 305a having mutually different diameters may be obtained by performing the fitting by using the circle fitting.

When a diameter of a circle is obtained from data having a shape of the circle including noise, in a case where the diameter of the circle is obtained by using the circle fitting, there is an advantage that the noise included in the shape of the circle may be averaged and removed.

In addition, when a peak includes an apex and a valley as in the electrocardiography signal, and a valley data portion is filled with noise, in a case where the circle fitting is used, there is an advantage that the diameter of the circle may be obtained by using only partial data of an apex having low noise.

The third module 233 may obtain a diameter of a circle formed on the fitted Nyquist diagram as the size of the electrocardiography signal. In this case, the diameter of the circle formed on the fitted Nyquist diagram may be proportional to sizes of a P wave, an R wave, and a T wave of the electrocardiography signal.

In detail, the third module 233 may be configured to: obtain a diameter of the first circle 305a corresponding to the first curve shape 305 formed at an earliest time among the curve shapes included in the Nyquist diagram created by the first module 231 as the size of the P wave of the electrocardiography signal; obtain a diameter of the second circle 303a corresponding to the second curve shape 303 formed at a later time than the first curve shape 305 as the size of the R wave of the electrocardiography signal; and obtain a diameter of the third circle 304a corresponding to the third curve shape 304 formed at a later time than the second curve shape 303 as the size of the T wave of the electrocardiography signal.

As shown in FIG. 3c, a diameter of a smallest-diameter circle 305a among the three circles included in the fitted Nyquist diagram may be the size of the P wave of the electrocardiography signal, a diameter of a middle-diameter circle 304a among the three circles included in the fitted Nyquist diagram may be the size of the T wave of the electrocardiography signal, and a diameter of a largest-diameter circle 303a among the three circles included in the fitted Nyquist diagram may be the size of the R wave of the electrocardiography signal.

Meanwhile, according to the present invention, the size of the P or T wave may be defined as a height from a baseline (see BL of FIG. 1a) of the electrocardiography signal to a peak of the P or T wave, and the size of the R wave may be defined as a height from a peak having a lower value between peaks of Q and S waves to a peak of the R wave.

As described above, according to one embodiment of the present invention, the electrocardiography signal may be Hilbert-transformed, and the size of the electrocardiography signal may be obtained based on the Hilbert-transformed electrocardiography signal, so that the sizes of the P, R, and T waves may be obtained with higher reliability than a scheme of obtaining sizes of P, R, and T waves by using a baseline BL.

Figure 4:
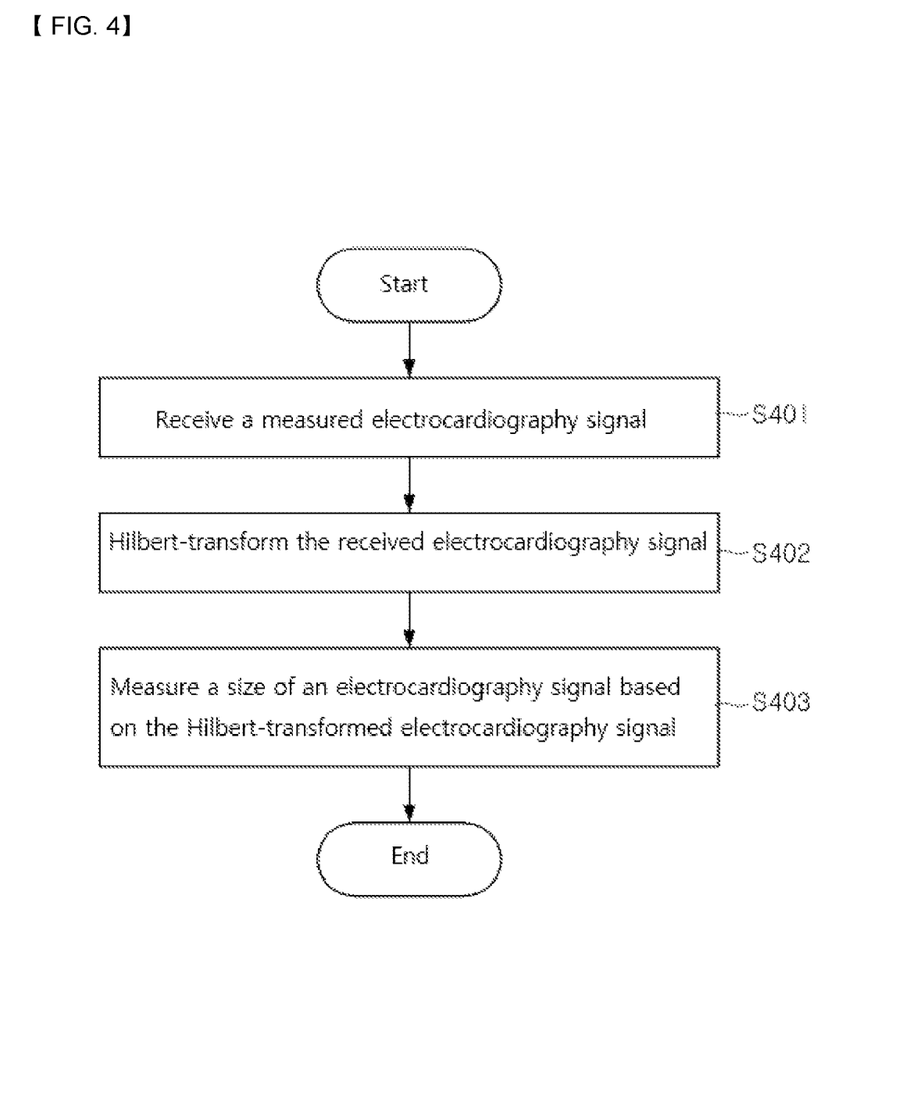
FIG. 4 is a flowchart for describing a method for measuring a size of an electrocardiography signal using a Hilbert transform according to one embodiment of the present invention.

Meanwhile, FIG. 4 is a flowchart for describing a method for measuring a size of an electrocardiography signal using a Hilbert transform according to one embodiment of the present invention.

Hereinafter, a method for measuring a size of an electrocardiography signal using a Hilbert transform according to one embodiment of the present invention will be described in detail with reference to FIGS. 1 to 4. However, for a concise description of the invention, redundant descriptions of the configurations that are previously described in FIGS. 1 to 3d will be omitted.

According to one embodiment of the present invention, the method for measuring the size of the electrocardiography signal using the Hilbert transform may start with receiving, by a receiving unit 210, a measured electrocardiography signal (S401). The received electrocardiography signal may be transmitted to a transform unit 220.

Next, the transform unit 220 may Hilbert-transform the received electrocardiography signal (S402).

Finally, a measurement unit 230 may measure the size of the electrocardiography signal based on the Hilbert-transformed electrocardiography signal (S403).

In detail, a first module 231 of the measurement unit 230 may create a Nyquist diagram, which is a time response curve in which a value of the electrocardiography signal is a real value and a value of the Hilbert-transformed electrocardiography signal is an imaginary value. The created Nyquist diagram may be transmitted to a second module 232. As described above, while a Nyquist diagram generally refers to a frequency response curve according to a frequency variation, the Nyquist diagram in the present invention refers to a time response curve according to a time variation.

Next, the second module 232 of the measurement unit 230 may fit the created Nyquist diagram by using circle fitting.

Finally, a third module 233 of the measurement unit 230 may obtain a diameter of a circle formed on the fitted Nyquist diagram as the size of the electrocardiography signal.

In detail, as described above, the third module 233 may be configured to: obtain a diameter of a first circle 305a corresponding to a first curve shape 305 formed at an earliest time among curve shapes included in the Nyquist diagram created by the first module 231 as a size of a P wave of the electrocardiography signal; obtain a diameter of a second circle 303a corresponding to a second curve shape 303 formed at a later time than the first curve shape 305 as a size of an R wave of the electrocardiography signal; and obtain a diameter of a third circle 304a corresponding to a third curve shape 304 formed at a later time than the second curve shape 303 as a size of a T wave of the electrocardiography signal.

As described above, according to one embodiment of the present invention, the electrocardiography signal may be Hilbert-transformed, and the size of the electrocardiography signal may be obtained based on the Hilbert-transformed electrocardiography signal, so that the sizes of the P, R, and T waves may be obtained with higher reliability than a scheme of obtaining sizes of P, R, and T waves by using a baseline BL.

In describing the present invention, the term "~ unit" may be implemented in various ways such as a processor, program instructions executed by a processor, a software module, a microcode, a computer program product, a logic circuit, an application-specific integrated circuit, and firmware.

The method for measuring the size of the electrocardiography signal using the Hilbert transform according to one embodiment of the present invention as described above may be produced as a program to be executed on a computer, and stored in a computer-readable recording medium. Examples of the computer-readable recording medium include a ROM, a RAM, a CD-ROM, a magnetic tape, a floppy disk, an optical data storage device, and the like. In addition, the computer-readable recording medium may be distributed to computer systems connected to each other through a network so that a computer-readable code may be stored and executed in a distributed manner. Further, functional programs, codes, and code segments for implementing the method may be easily inferred by programmers skilled in the art to which the present invention pertains.

The present invention is not limited to the above-described embodiments and the accompanying drawings. The scope of rights of the present invention is intended to be limited by the appended claims, and it will be apparent to those of ordinary skill in the art that various substitutions, modification, and changes may be made without departing from the technical idea of the present invention as defined in the claims.

The invention claimed is:

1. An apparatus for measuring a size of an electrocardiography signal using a Hilbert transform, the apparatus comprising:
   a receiving unit for receiving a measured electrocardiography signal;
   a transform unit for Hilbert-transforming the received electrocardiography signal; and
   a measurement unit for obtaining the size of the electrocardiography signal based on the Hilbert-transformed electrocardiography signal,
   wherein the measurement unit includes:
      a first module for creating a Nyquist diagram, which is a time response curve in which a value of the electrocardiography signal is a real value and a value of the Hilbert-transformed electrocardiography signal is an imaginary value;
      a second module for fitting the created Nyquist diagram by using circle fitting; and
      a third module for obtaining a diameter of a circle formed on the fitted Nyquist diagram as the size of the electrocardiography signal.

2. The apparatus of claim 1, wherein the diameter of the circle formed on the fitted Nyquist diagram is proportional to sizes of a P wave, an R wave, and a T wave of the electrocardiography signal.

3. The apparatus of claim 2, wherein the size of the P or T wave is a height from a baseline of the electrocardiography signal to a peak of the P or T wave, and
   the size of the R wave is a height from a peak having a lower value between peaks of Q and S waves to a peak of the R wave.

4. The apparatus of claim 1, wherein the third module is configured to:
   obtain a diameter of a first circle corresponding to a first curve shape formed at an earliest time among curve shapes included in the Nyquist diagram as a size of a P wave of the electrocardiography signal;
   obtain a diameter of a second circle corresponding to a second curve shape formed at a later time than the first curve shape as a size of an R wave of the electrocardiography signal; and
   obtain a diameter of a third circle corresponding to a third curve shape formed at a later time than the second curve shape as a size of a T wave of the electrocardiography signal.

5. A method for measuring a size of an electrocardiography signal using a Hilbert transform, the method comprising:
   a first step of receiving, by a receiving unit, a measured electrocardiography signal;
   a second step of Hilbert-transforming, by a transform unit, the received electrocardiography signal; and
   a third step of obtaining, by a measurement unit, the size of the electrocardiography signal based on the Hilbert-transformed electrocardiography signal,
   wherein the measurement unit includes:
      a first module for creating a Nyquist diagram, which is a time response curve in which a value of the electrocardiography signal is a real value and a value of the Hilbert-transformed electrocardiography signal is an imaginary value;
      a second module for fitting the created Nyquist diagram by using circle fitting; and
      a third module for obtaining a diameter of a circle formed on the fitted Nyquist diagram as the size of the electrocardiography signal.

6. A computer-readable recording medium recorded with a program to execute a method for measuring a size of an electrocardiography signal using a Hilbert transform, the method comprising:
   a first step of receiving, by a receiving unit, a measured electrocardiography signal;
   a second step of Hilbert-transforming, by a transform unit, the received electrocardiography signal; and
   a third step of obtaining, by a measurement unit, the size of the electrocardiography signal based on the Hilbert-transformed electrocardiography signal,
   wherein the measurement unit includes:
      a first module for creating a Nyquist diagram, which is a time response curve in which a value of the electrocardiography signal is a real value and a value of the Hilbert-transformed electrocardiography signal is an imaginary value;
      a second module for fitting the created Nyquist diagram by using circle fitting; and
      a third module for obtaining a diameter of a circle formed on the fitted Nyquist diagram as the size of the electrocardiography signal.

* * * * *